United States Patent
Moses et al.

(10) Patent No.: US 6,737,507 B2
(45) Date of Patent: May 18, 2004

(54) ANTIANGIOGENIC PEPTIDES AND COMPOSITIONS THEREOF

(75) Inventors: Marsha Moses, Brookline, MA (US); Inmin Wu, Boston, MA (US); Cecilia Fernandez, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 57 days.

(21) Appl. No.: 09/954,968

(22) Filed: Sep. 18, 2001

(65) Prior Publication Data

US 2002/0086420 A1 Jul. 4, 2002

Related U.S. Application Data

(63) Continuation of application No. PCT/US00/07156, filed on Mar. 17, 2000.
(60) Provisional application No. 60/125,020, filed on Mar. 18, 1999.

(51) Int. Cl.$^7$ ................................................ A61K 38/00
(52) U.S. Cl. ......................... 530/300; 514/12; 514/13; 514/14; 514/15; 530/324; 530/325; 530/326; 530/327; 530/328
(58) Field of Search ..................... 530/300, 324, 530/325, 326, 327, 328; 514/12, 13, 14, 15

(56) References Cited

U.S. PATENT DOCUMENTS

| 5,595,885 A | 1/1997 | Stetler-Stevenson et al. .... 435/69.2 |
| 5,698,671 A | 12/1997 | Stetler-Stevenson et al. .... 530/324 |

OTHER PUBLICATIONS

Takigawa et al., "Induction of Angiogenesis in Chick Yolk–Sac Membrane by Polyamines and its Inhibition by Tissue Inhibitors of Metalloproteinases (TIMP and TIMP–2)," *Biochemical and Biophysical Research Communications*, vol. 171, No. 3, pp. 1264–1271, 1990.

Valente et al., "TIMP–2 Over–Expression reduces Invasion and Angiogenesis and Protects B16F10 Melanoma Cells from Apoptosis," *Int. J. Cancer*, vol. 75, pp. 246–253, 1998.

*Primary Examiner*—Ulrike Winkler
(74) *Attorney, Agent, or Firm*—Nixon Peabody LLP

(57) ABSTRACT

The present invention provides an antiangiogenic polypeptide having the amino acid sequence set forth in SEQ ID NO: 1 or a portion thereof which is effective to inhibit endothelial cell proliferation as determined by the capillary EC proliferation assay. Preferably, the portion has at least 50% inhibition of bFGF-stimulated EC proliferation at 5 Tg/ml, more preferably 75% inhibition, most preferably 95% inhibition.

3 Claims, 2 Drawing Sheets

SEQUENCE LISTING

<160> NUMBER OF SEQ ID NOS: 8

<210> SEQ ID NO 1
<211> LENGTH: 67
<212> TYPE: PRT
<213> ORGANISM: Homo sapiens

<400> SEQUENCE: 1

```
Cys Leu Ile Thr Arg Cys Pro Met Ile Pro Cys Tyr Ile Ser Ser Pro
1               5                   10                  15

Asp Glu Cys Lys Trp Met Asp Trp Val Thr Glu Leu Asn Ile Asn Gly
            20                  25                  30

His Gln Ala Leu Phe Phe Ala Cys Ile Leu Arg Ser Asp Gly Ser Cys
        35                  40                  45

Ala Trp Tyr Arg Gly Ala Ala Pro Pro Leu Gln Glu Phe Lys Asp Ile
    50                  55                  60

Glu Asp Pro
65
```

<210> SEQ ID NO 2
<211> LENGTH: 10
<212> TYPE: PRT
<213> ORGANISM: Homo sapiens

<400> SEQUENCE: 2

```
Leu Ile Thr Arg Cys Pro Met Ile Pro Cys
1               5                   10
```

<210> SEQ ID NO 3
<211> LENGTH: 17
<212> TYPE: PRT
<213> ORGANISM: Homo sapiens

<400> SEQUENCE: 3

```
Leu Ile Thr Arg Cys Pro Met Ile Pro Cys Tyr Ile Ser Ser Pro Asp
1               5                   10                  15

Glu
```

<210> SEQ ID NO 4
<211> LENGTH: 40
<212> TYPE: PRT
<213> ORGANISM: Homo sapiens

<400> SEQUENCE: 4

```
Cys Leu Ile Thr Arg Cys Pro Met Ile Pro Cys Tyr Ile Ser Ser Pro
1               5                   10                  15

Asp Glu Cys Lys Trp Met Asp Trp Val Thr Glu Leu Asn Ile Asn Gly
            20                  25                  30

His Gln Ala Leu Phe Phe Ala Cys
        35                  40
```

<210> SEQ ID NO 5
<211> LENGTH: 22
<212> TYPE: PRT
<213> ORGANISM: Homo sapiens

<400> SEQUENCE: 5

```
Cys Lys Trp Met Asp Trp Val Thr Glu Leu Asn Ile Asn Gly His Gln
1               5                   10                  15
```

```
Ala Leu Phe Phe Ala Cys
            20

<210> SEQ ID NO 6
<211> LENGTH: 48
<212> TYPE: PRT
<213> ORGANISM: Homo sapiens

<400> SEQUENCE: 6

Cys Leu Ile Thr Arg Cys Pro Met Ile Pro Cys Tyr Ile Ser Ser Pro
1               5                  10                  15

Asp Glu Cys Lys Trp Met Asp Trp Val Thr Glu Leu Asn Ile Asn Gly
            20                  25                  30

His Gln Ala Leu Phe Phe Ala Cys Ile Leu Arg Ser Asp Gly Ser Cys
        35                  40                  45

<210> SEQ ID NO 7
<211> LENGTH: 19
<212> TYPE: PRT
<213> ORGANISM: Homo sapiens

<400> SEQUENCE: 7

Ala Trp Tyr Arg Gly Ala Ala Pro Pro Leu Gln Glu Phe Lys Asp Ile
1               5                  10                  15

Glu Asp Pro

<210> SEQ ID NO 8
<211> LENGTH: 194
<212> TYPE: PRT
<213> ORGANISM: Homo sapiens

<400> SEQUENCE: 8

Cys Ser Cys Ser Thr Val His Pro Gln Gln Ala Phe Cys Asn Ala Asp
1               5                  10                  15

Val Val Ile Arg Ala Leu Ala Val Ser Glu Leu Glu Val Asp Ser Gly
            20                  25                  30

Asn Asp Ile Tyr Gly Asn Pro Ile Leu Arg Ile Gln Tyr Glu Ile Leu
        35                  40                  45

Gln Ile Leu Leu Phe Leu Gly Ile Glu Leu Asp Ile Glu Phe Ile Tyr
    50                  55                  60

Thr Ala Pro Ser Ser Ala Val Cys Gly Val Glu Lys Asp Val Gly Gly
65                  70                  75                  80

Leu Leu Glu Tyr Lys Ile Ala Gly Leu Ala Glu Gly Asp Gly Leu Arg
                85                  90                  95

His Ile Thr Lys Cys Asp Phe Ile Val Pro Trp Asp Thr Lys Ser Thr
            100                 105                 110

Thr Gln Leu Leu Ser Lys Asn His Arg Tyr Gln Gln Gly Cys Glu Cys
        115                 120                 125

Leu Ile Thr Arg Cys Pro Met Ile Pro Cys Tyr Ile Ser Ser Pro Asp
    130                 135                 140

Glu Cys Lys Trp Thr Asp Trp Val Thr Glu Leu Asn Ile Asn Gly His
145                 150                 155                 160

Gln Ala Leu Phe Phe Ala Cys Ile Leu Arg Ser Asp Gly Ser Cys Ala
                165                 170                 175

Trp Tyr Arg Gly Ala Ala Pro Pro Leu Gln Glu Phe Lys Asp Ile Glu
            180                 185                 190

Asp Pro
```

ANTIANGIOGENIC PEPTIDES AND COMPOSITIONS THEREOF

BACKGROUND OF THE INVENTION

The following application is a continuation of PCT/US00/07156, filed Mar. 17, 2000, which is an international filing of provisional application No. 60/125,020, filed Mar. 18, 1999.

FIELD OF THE INVENTION

The present invention provides for novel antiangiogenic polypeptides and method of use thereof for treatment of diseases or disorders involving abnormal angiogenesis and tissue remodeling-associated conditions.

BACKGROUND

Blood vessels are the means by which oxygen and nutrients are supplied to living tissues and waste products are removed from living tissue. Angiogenesis refers to the process by which new blood vessels are formed. See, for example, the review by Folkman and Shing, *J. Biol. Chem.* 267, 10931–10934 (1992). Thus, where appropriate, angiogenesis is a critical biological process. It is essential in reproduction, development and wound repair. However, inappropriate angiogenesis can have severe negative consequences. For example, it is only after many solid tumors are vascularized as a result of angiogenesis that the tumors have a sufficient supply of oxygen and nutrients that permit it to grow rapidly and metastasize. Because maintaining the rate of angiogenesis in its proper equilibrium is so critical to a range of functions, it must be carefully regulated in order to maintain health. The angiogenesis process is believed to begin with the degradation of the basement membrane by proteolytic enzymes, e.g., metalloproteinases (MMPs) and plasminogen activator (PA), secreted from endothelial cells (EC) activated by mitogens such as vascular endothelial growth factor (VEGF) and basic fibroblast growth factor (bFGF).

Proteolytic activity is also required for the migration of EC into the perivascular stroma. These events are followed by sprout extension and subsequent lumen formation (Ausprunk, D. H., et al., *Microvascular Res.* 14:53–65 (1977)). As is EC "escape" from the parent venule, capillary sprout elongation, lumen formation, and EC migration are all events which are dependent on a shift in the proteolytic balance in favor of enzymatic activity (Ausprunk, D. H., et al., *Microvascular Res.* 14:53–65 (1977), Kalebic, T., et al. *Science,* 221:281–283 (1983), and (Moses, M. A., et al., *Science* 248:1408–1410 (1990)). Vascular morphogenesis and invasion are also regulated by shifts in the finely tuned balance between proteases and their inhibitors (Liotta, L. A., et al., *Cell* 64:327–336, (1991); Moses, M. A., et al.,*J. Cell Biochem.* 47:1–8 (1991); Herron, G. S., et al.,*J. Biol. Chem.* 261:2814–2828 (1986), and Montesano, R., et. al., *Cell* 62:435–445, (1990)).

An accumulating body of evidence suggests that the remodeling of ECM that occurs during normal growth, wound repair and angiogenesis as well as during the development and progression of pathologic conditions including malignant diseases, is accomplished largely through the action of MMPs (Birkedal-Hansen, H. *Cell. Bio.* 7:728–735 (1985), Matrisian, L. *Trends Genet.* 6:121–125, (1990), and Woessner, J. F.*Acad. Sci.* 732:11–21 (1994), and Woessner, J. F. *Ann. N.Y. Acad. Sci.* 732:11–21, 1994.

The MMPs are members of a multigene family of metal-dependent enzymes. These proteases have been classified into four broad categories originally based on substrate specificity. These specific enzymes are the collagenases (MMP-1/EC3.4.24.7; MMP-8/EC3.4.24.34;MMP-13), the gelatinases A(MMP-2/EC3.4.24.24) and B(MMP-9/EC3.4.24.35), the stromelysins (MMP-3/EC3.4.24.17:MMP-10/EC3.4.24.22; MMP-1/EC3.4.24.7) including a metalloelastase (MMP-12), the membrane MMPs (MMP-14) (Birkedai-Hansen, H. *Current Opinions in Cell Biol.* 7:728–735, 1995. Matrisian, L. *Trends Genet.* 6:121–125, 1990. Woessner, J. F. *Ann. N.Y. Acad. Sci.* 732:11–21, 1994) and the family of membrane type MMPs (MT-MMP 1–4).

The regulation of MMP activity occurs at several levels including gene transcriptional control, proenzyme activation and inhibition of activated MMPs by endogenous inhibitors. Like many other enzyme families, the MMPs are a key component of a system of "balanced proteolysis" wherein a finely tuned equilibrium exists between the amount of active enzyme and its proteinase inhibitor(s) (Liotta, L. A., et al., *Cell* 64:327–336, (1991)). These native metalloproteinase inhibitors comprise a family of proteins generally referred to as the TIMPS (Tissue Inhibitor of MetalloProteinase) (Docherty, A. J. P., et al., *Nature* 318:66–69, (1985), Carmichael, D. F., et al. *Proc. Natl. Acad. Sci. USA* 83:2407–2411, (1986); Moses, M. A., et al., *J. Cell. Biochem.* 47:230–235, (1991); Murray, J. B., et al., *J. Biol. Chem.* 261:4154–4159 (1986); Stetler-Stevenson, W. G., et al., *J. Biol. Chem.* 29:17374–17378, (1989); Pavloff, N., et al.,*J. Biol. Chem.* 267:17321–17326, (1992), and DeClerck, T. A., et al.,*J. Biol. Chem.* 264:17445–17453 (1989)). They bind to activate MMPs with 1:1 molar stoichiometry. There are also a number of less well-characterized lower molecular weight metalloproteinase inhibitors which await complete purification and identification.

The TIMPs consist of six disulfide-bonded loops. Deletion mutagenesis studies have demonstrated that two structurally distinct domains can be defined, the N-terminal domain consisting of loops 1–3 and the C-terminal domain consisting of loops 4–6 (Murphy, G. Houbrechts., et al. *Biochemistry* 30(33):8097–8101, (1991); Willenbrock, F., et al., *Biochem.* 32:4330–4337, (1993), and Nguyen, Q., et al., *Biochem.* 33:2089–2095, (1994)).

Much research attention has been focused on studies aimed at defining the domains of TIMPs that are important to their ability to inhibit MMP activity. Construction of truncated forms of these molecules has provided some insight. Residues 1–126 of TIMP-1 and 1–127 of TIMP-2 which contain three of the six disulfide bonds in the full-length molecules have been expressed in mammalian cells in the absence of the C-terminal region and are secreted in a soluble form (Murphy, G., et al. *Biochemistry* 30(33):8097–8101, (1991)). These truncated forms inhibit matrilysin and the catalytic domains of stromelysin and gelatinase A, demonstrating that there is a direct interaction between the N-terminal domain of the TIMPs and the catalytic domains of the MMPs (Murphy, G., et al. *Biochemistry* 30(33):8097–8101, (1991); Willenbrock, F., et al., *Biochem.* 32:4330–4337, (1993), and Nguyen, Q., et al., *Biochem.* 33:2089–2095, (1994). The structure of the N-terminal domain of either TIMP-1 or TIMP-2 is not affected by the C-terminal domain (Nguyen. Q., et al., *Biochemistry* 33:2089–2095, (1994)).

A significant number of mutational analyses also support the concept that the $NH_2$-terminal domain of TIMP-1 ($Cys^1$-$Glu^{126}$) is sufficient for inhibition of MMPs (Wilheim, S. M., et al.,*J. Biol. Chem.* 264:17213–17221, (1989), Murphy, G., et al., *Biochemistry* 30(33):8097–8101, (1991); Murphy, G., et al., *Bio. Chem. Biophys. Acta.* 839:214–218, (1985); Stricklin, G. P., *Collagen Relat. Res.* 6:219–228, (1986); Tolley, S. P., et al., *Protein: Struc., Fuct., Genet.* 17:435–437, (1993), and Howard, E. W., et al., *J. Biol. Chem.* 266:13064–13069, (1991)). Furthermore, single-residue mutations in the region bounded by Cys3 and Cys13 caused an increase of 8-fold in K/when compared with wild type TIMP-1 (O'Shea, M., et al., *Biochemistry* 31(42): 10146–10151, (1992)). A series of experiments including competition studies with synthetic peptides and localization of epitopes of blocking antibodies revealed that the region marking the transition between the NH2-terminal and COOH-terminal domains of the TIMP-1 molecule may be particularly important for its ability to inhibit collagenase (Bodden, M. K., et al., *J. Biol. Chem.* 269:18943–18952, (1994)).

It is now widely accepted that the N-terminal domain of the TIMPs represent a stable, minimized form of the inhibitor that includes the major site or sites necessary for MMP inhibition (Williamson, R. A., et al., *Biochem.* 33:11745–11759, (1994)). Site-directed mutagenesis studies on TIMP-1 have demonstrated that no single residue is likely to be responsible for MMP inhibition (O'Shea, M., et al., *Biochem.* 10146–10151, (1992)).

The C-terminal domain of TIMPs also makes some binding contribution to the TIMP-MMP complex, in particular, the C-terminal domain of TIMP-2 which may be responsible for the specific interaction of this molecule with progelatinase A (Willenbrock, F., et al., *Biochemistry* 32:4330–4337, (1993)). Mutational studies also support the idea that the COOH-terminal domain of TIMP-2 which does not appear to be required for MMP inhibition (O'Shea, M., et al., *Biochemistry* 31(42):10146–10151 (1992)) interacts with the pexin-like domain of gelatinase A (Hayakawa, T., et al., *FEBS Lett.* 298:29–32, (1992)). This interaction has been shown to prevent autodegradation of the enzyme (Goldberg, G. I., et al., *J. Biol. Chem.* 267:4583–4591 (1992), Bodden, M. K., et al., *Biol. Chem.* 269:18943–18952, (1994), and Howard, E. W., et al., *J. Biol. Chem.* 266:13084–13089, (1991)). The C-terminal domain of both TIMP-1 and TIMP-2 participate in low-affinity interactions with the C-terminal domain of gelatinase A which increases the rate of association by a factor of about 100 in both cases (Willenbrock, F., et al., *Biochemistry* 32:4330–4337, (1993)).

TIMPs have been shown to inhibit the migration of endothelial cells in vitro and, depending on the model used, angiogenesis in vivo. (Mignatti, et al. *J. Cell Bio.* 108:671–682, (1989)) first demonstrated that TIMP-1 could inhibit migration of microvascular cells in vitro using the amnion invasion assay. Montesano and coworkers later showed that a collagenase inhibitor (1,10-phenanthroline) could inhibit capillary tube formation in vitro (Montesano, R., et. al. *Cell* 42:489–477, (1985)). Since it was first demonstrated that a TIMP purified from a vascular cartilage was a potent inhibitor of angiogenesis in vivo and EC proliferation and migration in vitro (Moses, M. A., et al., *Science* 248:1408–1410, (1990); Moses, M. A., et al., *J. Cell Biol.* 119:475–482, (1992) and Murphy, A. N. et al., *J. Cell. Phys.* 157:351–358 (1993)) showed that TIMP-2, but not TIMP-1, inhibited FGF-stimulated endothelial cell proliferation. TIMP-1 has been shown to stimulate the growth of EC proliferation in other studies as well (Hayakawa, T., et al *FEBS Letts.* 298:29–32, (1992)). TIMPs have been shown to inhibit neovascularization in various in vivo models (Takigawa, M., et al., *Biochem. Biophys. Res. Commun.* 171:1264–1271 and Johnson, M. D. et al., *J. Cell. Physiol.* 160:194–202, (1989)).

Much research attention has focused on studies aimed at defining the domain of TIMPs that are important to their ability to inhibit MMP activity. It is now widely accepted that the N-terminal domain of the TIMPs represents a stable, minimized form of the inhibitor that includes the major site or sites necessary for MMP inhibition (Williamson, R. A. et al. *Biochemistry* 33:11745–11759 (1994)). The C-terminal domain of TIMPs also makes some binding contribution to the TIMP-MMP complex, in particular, the C-terminal domain of TIMP-2 which may be responsible for the specific interaction of this molecule with progelatinase A (Willenbrock, F. et al., *Biochemistry* 32:4330–4337 (1993)).

It has been suggested that the regions of amino acid sequences between TIMP-1 and TIMP-2 that are highly conserved such as the N-terminus, may be responsible for the known shared functions of these proteins, for example, inhibition of activated MMPs and their shared ability to inhibit FGF-stimulated capillary EC migration (Moses, M. A. et al., *Science* 248:1408–1410 (1990); Moses, M. A. et al., *J. Cell Biol.* 119:475–482 (1992); Mignatti, P. et al., *J. Cell Bio.* 108:671–682 (1989) and Murphy, A. N. et al., *J. Cell. Phys.* 157:351–358 (1993)). Areas of low homology, for example, the C-terminus, may be responsible for those functions which are unique for the individual TIMPs (Stetler-Stevenson et al., *J. Biol. Chem.* 265(23) 13933–13936 (1990)). These include the binding of TIMP-2 to the latent form of gelatinase A and the failure of TIMP-2 antibodies to detect TIMP-1 (Stetler-Stevenson, W. G. et al., *J. Biol. Chem.* 265(23):13933–13936 (1990).

The rate of angiogenesis involves a change in the local equilibrium between positive and negative regulators of the growth of microvessels. The therapeutic implications of angiogenic growth factors were first described by Folkman and colleagues over two decades ago (Folkman, *N. Engl. J. Med.*, 285:1182–1186 (1971)). Abnormal angiogenesis occurs when the body loses at least some control of angiogenesis, resulting in either excessive or insufficient blood vessel growth. For instance, conditions such as ulcers, strokes, and heart attacks may result from the absence of angiogenesis normally required for natural healing. In contrast, excessive blood vessel proliferation can result in tumor growth, tumor spread, blindness, psoriasis and rheumatoid arthritis.

Thus, there are instances where a greater degree of angiogenesis is desirable—increasing blood circulation, wound healing, and ulcer healing. For example, recent investigations have established the feasibility of using recombinant angiogenic growth factors, such as fibroblast growth factor (FGF) family (Yanagisawa-Miwa, et al., *Science,* 257:1401–1403 (1992) and Baffour, et al., *J Vasc Surg,* 16:181–91 (1992)), endothelial cell growth factor (ECGF)(Pu, et al., *J Surg Res,* 54:575–83 (1993)), and more recently, vascular endothelial growth factor (VEGF) to expedite and/or augment collateral artery development in animal models of myocardial and hindlimb ischemia (Takeshita, et al., *Circulation,* 90:228–234 (1994) and Takeshita, et al., *J Clin Invest,* 93:662–70 (1994)).

Conversely, there are instances, where inhibition of angiogenesis is desirable. For example, many diseases are driven by persistent unregulated angiogenesis, also sometimes referred to as "neovascularization." In arthritis, new capillary blood vessels invade the joint and destroy cartilage. In diabetes, new capillaries invade the vitreous, bleed, and cause blindness. Ocular neovascularization is the most common cause of blindness. Tumor growth and metastasis are angiogenesis-dependent. A tumor must continuously stimulate the growth of new capillary blood vessels for the tumor itself to grow.

The current treatment of these diseases is inadequate. Agents which prevent continued angiogenesis, e.g, drugs (TNP-470), monoclonal antibodies, antisense nucleic acids and proteins (angiostatin and endostatin) are currently being tested. See, Battegay, *J. Mol. Med.*, 73, 333–346 (1995); Hanahan et al., *Cell*, 86, 353–364 (1996); Folkman, *N. Engl. J. Med.*, 333, 1757–1763 (1995). Although preliminary results with the antiangiogenic proteins are promising, they are relatively large in size and they are difficult to use and produce. Moreover, proteins are subject to enzymatic degradation. Thus, new agents that inhibit angiogenesis are needed. New antiangeogenic peptides that show improvement in size, ease of production, stability and/or potency would be desirable.

SUMMARY OF THE INVENTION

We have discovered that suprisingly peptide fragments of the carboxy terminus of TIMP-2 comprising no more than 35% of the TIMP-2 protein, do not inhibit MMP activity but have endothelial cell inhibitory activity, i.e., the ability to inhibit endothelial cell migration and proliferation. Thus these fragments are useful as antiangiogenic agents.

The present invention provides an antiangiogenic polypeptide having the following amino acid sequence CKITRCPMIPCYISSPDECLWMDWVTEKNINGHQAKFFACIKRSDGSCAWYRGA APPKQEFLDIEDP (SEQ ID NO: 1) or a portion thereof which is effective to inhibit endothelial cell proliferation as determined by the capillary EC proliferation assay. Preferably, the portion has at least 50% inhibition of bFGF-stimulated EC proliferation at 5 ug/ml, more preferably 75% inhibition, most preferably 95% inhibition.

Preferred antiangiogenic polypeptides of the invention include: KITRCPMIPC (SEQ ID NO: 2) (aa 129–138; partial loop-4+loop-5); KITRCPMIPCYISSPDE (SEQ ID NO: 3) (aa 129–145; partial loop-4+loop-5); CKITRCPMIPCYISSPDECLWMDWVTEKNINGHQAKFFAC (SEQ ID NO: 4) (aa 128–167; partial loop-4+loop-5+loop-6); CLWMDWVTEKNINGHQAKFFAC(SEQ ID NO: 5) (aa 146–167; loop-5); CKITRCPMIPCYISSPDECLWMDWVTEKNINGHQAKFFACIKRSDGSC (SEQ ID NO: 6) (AA 128–175; loop-4+loop-5+loop-6); and AWYRGAAPPKQEFLDIEDP (SEQ ID NO: 7)(aa 176–194).

The present invention further provides an antiangiogenic polypeptide comprising the amino acid sequence KITRCPMIPC (SEQ ID NO: 2), but excluding the full sequence of human TIMP-2 (SEQ ID NO:8, U.S. Pat. No. 5,595,885).

The present invention also provides pharmaceutical compositions comprising antiangiogenic polypeptides or nucleic acids encoding such a polypeptide, in therapeutically effective amounts that are capable of inhibiting endothelial cell proliferation, and their methods of use.

The invention further provides treatment of neovascular disorders by administration of a pharmaceutical composition comprising an antiangiogenic polypeptide of the invention or nucleic acid encoding such a polypeptide, and a pharmaceutically acceptable carrier.

The invention also provides for treatment of a class of disorders characterized as tissue remodeling-associated conditions, which include cancers, arthritic conditions, obstructive disorders, degenerative disorders, and problematic wound-healing and ulcerative disorders.

In one embodiment, a pharmaceutical composition of the invention is administered to treat a cancerous condition, or to prevent progression from the pre-neoplastic or pre-malignant state into a neoplastic or a malignant state. In other specific embodiments, a pharmaceutical composition of the invention is administered to treat ocular disorders associated with neovascularization.

Other aspects of the invention are disclosed infra.

DETAILED DESCRIPTION OF THE INVENTION

Figure 1:
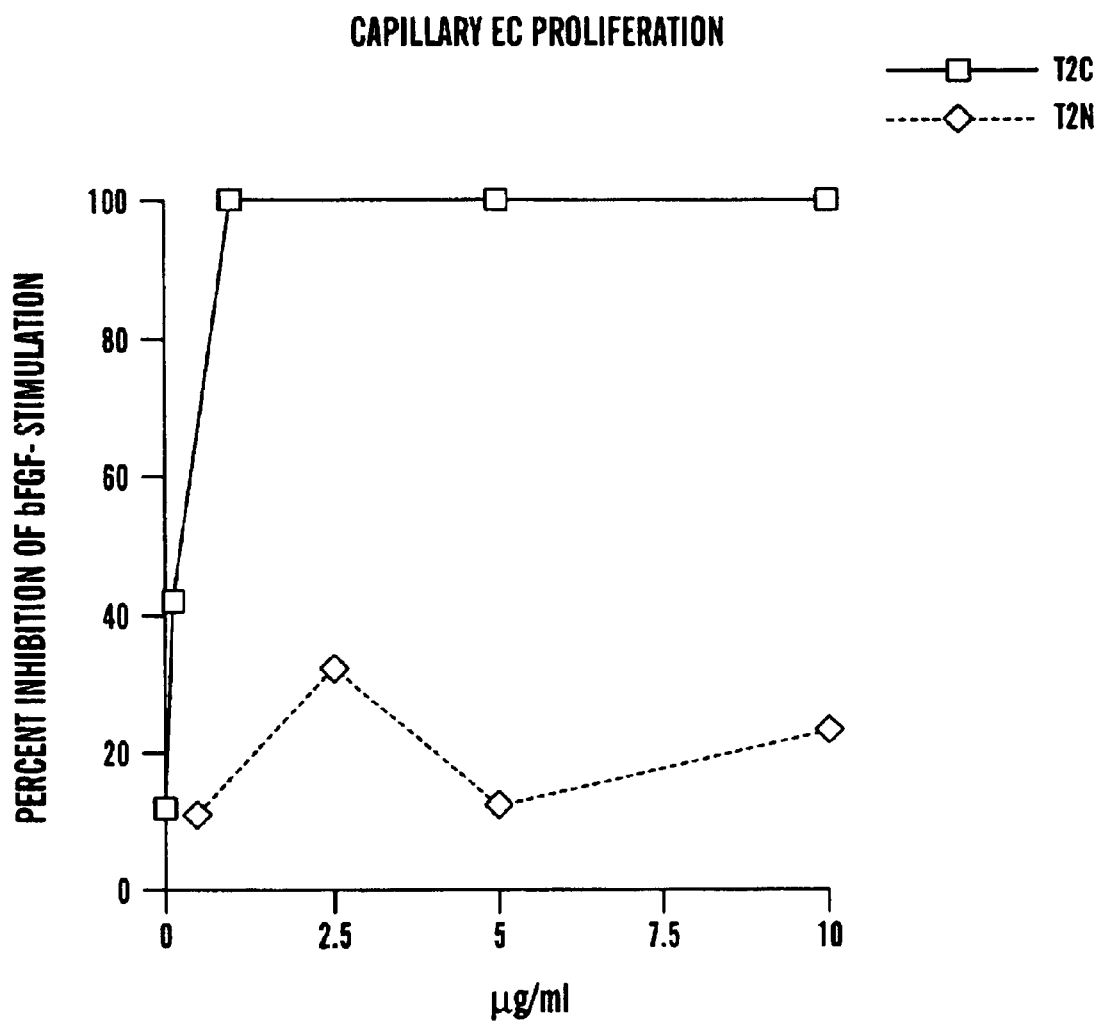
FIG. 1: bFGF-stimulated EC proliferation assay.

The present invention provides an antiangiogenic polypeptide having the amino acid sequence set forth in SEQ ID NO: 1 or a portion thereof which is effective to inhibit endothelial cell proliferation as determined by the capillary EC proliferation assay. Preferably, the portion has at least 50% inhibition of bFGF-stimulated EC proliferation at 5 Tg/ml, more preferably 75% inhibition, most preferably 95% inhibition.

Preferred antiangiogenic polypeptides of the invention include: KITRCPMIPC (SEQ ID NO: 2) (aa 129–138; partial loop-4+loop-5); KITRCPMIPCYISSPDE (SEQ ID NO: 3) (aa 129–145; partial loop-4+loop-5); CKITRCPMIPCYISSPDECLWMDWVTEKNINGHQAKFFAC (SEQ ID NO: 4) (aa 128–167; partial loop-4+loop-5+loop-6); CLWMDWVTEKNINGHQAKFFAC(SEQ ID NO: 5) (aa 146–167; loop-5); CKITRCPMIPCYISSPDECLWMDWVTEKNINGHQAKFFACIKRSDGSC (SEQ ID NO: 6) (AA 128–175; loop-4+loop-5+loop-6); and AWYRGAAPPKQEFLDIEDP (SEQ ID NO: 7)(aa 176–194).

The present invention further provides an antiangiogenic polypeptide comprising the amino acid sequence KITRCPMIPC (SEQ ID NO: 2), but excluding the full sequence of human TIMP-2 (SEQ ID NO:8, U.S. Pat. No. 5,595,885).

Antiangiogenic polypeptides of the invention can be combined with a therapeutically effective amount of another molecule which negatively regulates angiogenesis which may be, but is not limited to, platelet factor 4, thrombospondin-1, tissue inhibitors of metalloproteases, prolactin (16-Kd fragment), angiostatin (38-Kd fragment of plasminogen), endostatin, bFGF soluble receptor, transforming growth factor beta, interferon alfa, and placental proliferin-related protein.

An antiangiogenic polypeptide of the invention may also be combined with chemotherapeutic agents.

Analogs of the antiangiogenic polypeptides of the invention can be made by altering the protein sequences by substitutions, additions or deletions that provide for functionally equivalent molecules. These include altering sequences in which functionally equivalent amino acid residues are substituted for residues within the sequence resulting in a silent change. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, praline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The antiangiogenic polypeptides and analogs of the invention can be derived from tissue or produced by various methods known in the art. The manipulations, which result in their production, can occur at the gene or protein level. For example, a cloned gene sequence coding for an antiangiogenic polypeptide can be modified by any of numerous strategies known in the art. Sambrook et al., 1990, Molecular Cloning, A Laboratory Manual, 2d ea., Cold Spring Harbor Laboratory, Cold Spring Harbor, N.Y. The sequence can be cleaved at appropriate sites with restriction endonuclease(s), followed by further enzymatic modification if desired, isolated, and ligated in vitro. In the production of the gene encoding a derivative or analog, care should be taken to ensure that the modified gene remains within the same translational reading frame as the troponin subunit gene, uninterrupted by translational stop signals, in the gene region where the desired troponin activity is encoded.

The antiangiogenic polypeptides are preferably produced by recombinant methods, including, for example, the yeast expression system *Pichia pastoris*. See the procedures disclosed in Example 1, which follows.

The term "isolated" means that the polypeptide is removed from its original environment. For example, a naturally-occurring polynucleotide or polypeptide present in a living animal is not isolated, but the same polynucleotide or DNA or polypeptides, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

Where it is desired to express a polypeptide of the invention any suitable system can be used. The general nature of suitable vectors, expression vectors and constructions therefor will be apparent to those skilled in the art.

Suitable expression vectors may be based on phages or plasmids, both of which are generally host-specific, although these can often be engineered for other hosts. Other suitable vectors include cosmids and retroviruses, and any other vehicles, which may or may not be specific for a given system. Control sequences, such as recognition, promoter, operator, inducer, terminator and other sequences essential and/or useful in the regulation of expression, will be readily apparent to those skilled in the art.

Correct preparation of nucleotide sequences may be confirmed, for example, by the method of Sanger et al. (*Proc. Natl. Acad. Sci. USA* 74:5463–7 (1977)).

A DNA fragment encoding an antiangiogenic polypeptide may readily be inserted into a suitable vector. Ideally, the receiving vector has suitable restriction sites for ease of insertion, but blunt-end ligation, for example, may also be used, although this may lead to uncertainty over reading frame and direction of insertion. In such an instance, it is a matter of course to test transformants for expression, 1 in 6 of which should have the correct reading frame. Suitable vectors may be selected as a matter of course by those skilled in the art according to the expression system desired.

By transforming a suitable organism or, preferably, eukaryotic cell line, such as HeLa, with the plasmid obtained, selecting the transformant with ampicillin or by other suitable means if required, and adding tryptophan or other suitable promoter-inducer (such as indoleacrylic acid) if necessary, the desired polypeptide or protein may be expressed. The extent of expression may be analyzed by SDS polyacrylamide gel electrophoresis-SDS-PAGE (Lemelli, *Nature* 227:680–685 (1970)).

Suitable methods for growing and transforming cultures etc. are usefully illustrated in, for example, *Molecular Cloning, A Laboratory Manual* (2nd Ed., Sambrook, Fritsch and Maniatis, Cold Spring Harbor), *Current Protocols in Molecular Biology* (Eds. Aufubel, Brent, Kingston, More, Feidman, Smith and Stuhl, Greene Publ. Assoc., Wiley-Interscience, NY, N.Y. 1992).

The polypeptides and proteins may be isolated from the fermentation or cell culture and purified using any of a variety of conventional methods including: liquid chromatography such as normal or reversed phase, using HPLC, FPLC and the like; affinity chromatography (such as with inorganic ligands or antibodies); size exclusion chromatography; immobilized metal chelate chromatography; gel electrophoresis; and the like. One of skill in the art may select the most appropriate isolation and purification techniques without departing from the scope of this invention.

The polypeptides may be generated by any of several chemical techniques. For example, they may be prepared using the solid-phase synthetic technique originally described by R. B. Merrifield, "Solid Phase Peptide Synthesis. I. The Synthesis Of A Tetrapeptide", J. Am. Chem. Soc., 83, pp. 2149–54 (1963), or they may be prepared by synthesis in solution. A summary of peptide synthesis techniques may be found in E. Gross & H. J. Meinhofer, The Peptides: Analysis, Synthesis, Biology; Modern Techniques Of Peptide And Amino Acid Analysis, John Wiley & Sons, (1981) and M. Bodanszky, Principles Of Peptide Synthesis, Springer-Verlag (1984).

The functional activity and/or therapeutically effective dose of an antiangiogenic polypeptide or nucleic acid encoding therefor can be assayed in vitro by various methods. For example, where one is assaying for the ability of the angiogenic inhibitory polypeptides, fragments, and analogs, to inhibit or interfere with the proliferation of capillary endothelial cells (EC) in vitro, various bioassays known in the art can be used, including, but not limited to, radioactive incorporation into nucleic acids, calorimetric assays and cell counting.

Inhibition of endothelial cell proliferation may be measured by calorimetric determination of cellular acid phosphatase activity or electronic cell counting. These methods provide a quick and sensitive screen for determining the number of endothelial cells in culture after treatment with the connective tissue growth factor protein, derivative, or analog of the invention, and an angiogenesis stimulating factor such as aFGF. The calorimetric determination of cellular acid phosphatase activity is described by Connolly et al., 1986, *J. Anal. Biochem.* J52:136–140. According to this method, capillary endothelial cells are treated with angiogenesis stimulating factors, such as aFGF, and a range of potential inhibitor concentrations. These samples are incubated to allow for growth, and then harvested, washed, lysed in a buffer containing a phosphatase substrate, and then incubated a second time. A basic solution is added to stop the reaction and color development is determined at 405 $\lambda$. According to Connolly et al., a linear relationship is obtained between acid phosphatase activity and endothelial cell number up to 10,000 cells/sample. Standard curves for acid phosphatase activity are also generated from known cell numbers in order to confirm that the enzyme levels reflect the actual EC numbers. Percent inhibition is determined by comparing the cell number of samples exposed to stimulus with those exposed to both stimulus and inhibitor.

The incorporation of radioactive thymidine by capillary endothelial cells represents another means by which to assay for the inhibition of endothelial cell proliferation by a potential angiogenesis inhibitor. According to this method, a predetermined number of capillary endothelial cells are grown in the presence of 3H-Thymidine stock, an angiogenesis stimulator such as for example, bFGF, and a range of concentrations of the angiogenesis inhibitor to be tested. Following incubation, the cells are harvested and the extent of thymidine incorporation is determined.

The ability of varying concentrations of antiangiogenic polypeptides to interfere with the process of capillary endothelial cell migration in response to an angiogenic stimulus can be assayed using the modified Boyden chamber technique.

Another means by which to assay the functional activity of antiangiogenic polypeptides involves examining the ability of the compounds to inhibit the directed migration of capillary endothelial cells which ultimately results in capillary tube formation. This ability may be assessed for example, using an assay in which capillary endothelial cells plated on collagen gels are challenged with the inhibitor, and determining whether capillary-like tube structures are formed by the cultured endothelial cells.

Assays for the ability to inhibit angiogenesis in vivo include the chick chorioallantoic membrane assay and mouse, rat or rabbit corneal pocket assays. See, Polverini et al., 1991, *Methods Enzymol.* 198:440–450. In corneal pocket assays, a tumor of choice is implanted into the cornea of the test animal in the form of a corneal pocket. The potential angiogenesis inhibitor is applied to the corneal pocket and the corneal pocket is routinely examined for neovascularization.

The ability of the antiangiogenic polypeptides to influence angiogenesis can also be determined using a number of known in vivo and in vitro assys. Such assays are disclosed in Jain et al., *Nature Medicine* 3, 1203–1208(1997), the disclosure of which is herein incorporated by reference.

The therapeutically effective dosage for inhibition of angiogenesis in vivo, defined as inhibition of capillary endothelial cell proliferation, migration, and/or blood vessel growth, may be extrapolated from in vitro inhibition assays using the compositions of the invention above or in combination with other angiogenesis inhibiting factors. The effective dosage is also dependent on the method and means of delivery. For example, in some applications, as in the treatment of psoriasis or diabetic retinopathy, the inhibitor is delivered in a topical-ophthalmic carrier. In other applications, as in the treatment of solid tumors, the inhibitor is delivered by means of a biodegradable, polymeric implant. The protein can also be modified, for example, by polyethyleneglycol treatment.

Diseases, disorders, or conditions, associated with abnormal angiogenesis or neovascularization, and can be treated with a theraputic compound of the invention include, but are not limited to retinal neovascularization, tumor growth, hemagioma, solid tumors, leukemia, metastasis, psoriasis, neovascular glaucoma, diabetic retinopathy, arthritis, endometriosis, and retinopathy of prematurity ROP).

The term "effective amount" refers to an amount of the antiangiogenic polypeptide of the invention sufficient to exhibit a detectable therapeutic effect. The therapeutic effect may include, for example, without limitation, inhibiting the growth of undesired tissue or malignant cells, inhibiting inappropriate angiogenesis (neovascularization), limiting tissue damage caused by chronic inflammation, inhibition of tumor cell growth, and the like. The precise effective amount for a subject will depend upon the subject's size and health, the nature and severity of the condition to be treated, and the like. Thus, it is not possible to specify an exact effective amount in advance. However, the effective amount for a given situation can be determined by routine experimentation based on the information provided herein.

The term "pharmaceutically acceptable" refers to compounds and compositions which may be administered to mammals without undue toxicity. Exemplary pharmaceutically acceptable salts include mineral acid salts such as hydrochlorides, hydrobromides, phosphates, sulfates, and the like; and the salts of organic acids such as acetates, propionates, malonates, benzoates, and the like.

The antiangiogenic polypeptides of the invention are administered orally, topically, or by parenteral means, including subcutaneous and intramuscular injection, implantation of sustained release depots, intravenous injection, intranasal administration, and the like. Accordingly, antiangiogenic polypeptides of the invention are preferably administered as a pharmaceutical composition comprising an antiangiogenic polypeptides of the invention in combination with a pharmaceutically acceptable carrier. Such compositions may be aqueous solutions, emulsions, creams, ointments, suspensions, gels, liposomal suspensions, and the like. Suitable carriers (excipients) include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol Registered TM, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, Silvadene Registered TM (Marion), Aquaphor Registered TM (Duke Laboratories), and the like. Other topical formulations include aerosols, bandages, and other wound dressings. Alternatively one may incorporate or encapsulate the theraputic compound of the invention in a suitable polymer matrix or membrane, thus providing a sustained-release delivery device suitable for implantation near the site to be treated locally. Other devices include indwelling catheters and devices such as the Alzet Registered TM minipump. Ophthalmic preparations may be formulated using commercially available vehicles such as Sorbi-care Registered TM (Allergan), Neodecadron Registered TM (Merck, Sharp & Dohme), Lacrilube Registered TM, and the like, or may employ topical preparations such as that described in U.S. Pat. No. 5,124,155, incorporated herein by reference. Further, one may provide a therapeutic compound of the invention in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in Remington's Pharmaceutical Sciences (Mack Pub. Co.).

The DNA encoding antiangiogenic polypeptides of the invention can be used in the form of gene therapy and delivered to a host by any method known to those of skill in the art to treat disorders associated with angiogenic or tissue remodeling-associated conditions.

A preferred embodiment of the present invention relates to methods of inhibiting angiogenesis of solid tumors to prevent further tumor growth and eventual metastasis. To this end, any solid tumor or the region surrounding the tumor accessible to gene transfer will be a target for the disclosed therapeutic applications. A DNA encoding an angiogenic polypeptide, housed within a recombinant viral- or nonviral-based gene transfer system may be directed to target cells within proximity of the tumor by any number of procedures known in the art, including but not limited to (a) surgical procedures coupled with administration of an effective amount of the DNA to the site in and around the tumor (involving initial removal of a portion or the entire tumor, if possible); (b) injection of the gene transfer vehicle directly into or adjacent to the site of the tumor; and, (c) localized or systemic delivery of the gene transfer vector and/or gene product using techniques known in the art.

Any solid tumor that contains angiogenic protein expressing cells will be a potential target for treatment. Examples, but by no means listed as a limitation, of solid tumors which will be particularly vulnerable to gene therapy applications are (a) neoplasms of the central nervous system such as, but again not necessarily limited to glioblastomas, astrocytomas, neuroblastomas, meningiomas, ependymomas; (b) cancers of hormone-dependent, tissues such as protstate, testicles, uterus, cervix, ovary, mammary carcinomas including but not limited to carcinoma in situ, medullary carcinoma, tubular carcinoma, invasive (infiltrating) carcinomas and mucinous carcinomas; (c) melanomas, including but not limited to cutaneous and ocular melanomas; (d) cancers of the lung which at least include squamous cell carcinoma, spindle carcinoma, small cell carcinoma, adenocarcinoma and large cell carcinoma; and (e) cancers of the gastrointestinal system such as esophageal, stomach, small intestine, colon, colorectal, rectal and anal region which at least include adenocarcinomas of the large bowel.

A DNA fragment encoding an antiangiogenic polypeptide may be delivered either systemically or to target cells in the proximity of a solid tumor of the mammalian host by viral or non-viral based methods. Viral vector systems which may be utilized in the present invention include, but are not limited to, (a) adenovirus vectors; (b) retrovirus vectors; (c) adeno-associated virus vectors; (d) herpes simplex virus vectors; (e) SV 40 vectors; (f) polyoma virus vectors; (g) papilloma virus vectors; (h) picornavirus vectors; and (i) vaccinia virus vectors.

The recombinant virus or vector containing the DNA encoding the antiangiogenic polypeptide of the present invention is preferably administered to the host by direct injection into a solid tumor and/or quiescent tissue proximal to the solid tumor, such as adipose or muscle tissue. It will of course be useful to transfect tumor cells in the region of targeted adipose and muscle tissue. Transient expression of the antiangiogenic polypeptide in these surrounding cells will result in a local extracellular increase in these proteins.

Non-viral vectors which are also suitable include DNA-lipid complexes, for example liposome-mediated or ligand/poly-L-Lysine conjugates, such as asialoglyco-protein-mediated delivery systems (see, e.g., Felgner et al., 1994, *J. Biol. Chem.* 269:2550–2561; Derossi et al., 1995, Restor. Neurol. Neuros. 8:7–10; and Abcallah et al., 1995, Biol. Cell 85:1–7). Direct injection of "naked" DNA may also be used.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The references cited throughout this application are herein incorporated by reference.

The present invention is further illustrated by the following Examples. These Examples are provided to aid in the understanding of the invention and are not construed as a limitation thereof.

EXAMPLES

Cloning and Expression of TIMP Domains

The yeast expression system *Pichia pastoris* (Invitrogen) was used to express full length TIMPs as well as various domains of these inhibitors. *Pichia pastoris* yeast expression has been successfully utilized to produce large quantities of disulfide-bonded proteins (White, C. E., et al. *Structure* 2:1003–1005, (1994)). This is of particular importance given the fact that the TIMPs contain 6 disulfide bonds which are highly conserved. This expression system has a number of significant advantages over others. First, proteins produced in *P. pastoris* are usually folded correctly because yeast provides an intracellular folding environment similar to that of mammalian cells. A number of disulfide-bonded proteins have now been successfully expressed in *P. pastoris* including epidermal growth factor, EGF (Clare, J. J., et al. *Gene* 105:205–212, (1991)), aprotinin (Vedvick, T., et al., *Indust. Microbiol.* 7:199–202, (1991)) as well as proteins requiring mammalian post-translational modifications, such as tumor necrosis factor (Sreekrishna, K., et al., *Biotechnology* 28:4117–4125, (1989)), invertase (Tschopp, J. J., et al., *Biotechnology* 5:1305–1308, (1987)) and others. Second, secretion of proteins into the medium surrounding *P. pastoris* yeast cells can be easily accomplished, providing a substantial improvement in purification over other methods. Third, high yields of protein per liter of culture (typically 100–500 mg/L) can be obtained from multicopy inserts when expression is carried out in a fermenter. Fourth, transformation and growth of *P. pastoris* does not require specials hoods, incubators or techniques other than those used for *E. coli*. Finally, spheroblast transformation produced multicopy insertion of the gene of interest, vastly increasing the yield of protein and it is easy to select for multicopy insert transformants (White, C. E., et. al., *Structure* 2:1003–1005, (1994)).

We successfully expressed full length human TIMP-3 in the *P. pastoris* system. Cloning vector PCR II carrying the full-length human TIMP-3 gene was subjected to digestion with restriction enzymes EcoR I and Not I to release the fragment of cDNA containing TIMP-3. Following gel extraction of the fragment, ligation was performed with the Pichia shuttle vector pPIC9K (Invitrogen) digested with EcoR I and Not I. Aliquots of the ligation mixture were used to transform competent *E. coli* XL2-Blue. Minipreps of the resulting clones were analyzed by restriction analysis using EcorR I and Not I. A construct having the correct orientation was designated TIMP3-pPICK. This recombinant plasmid was then linearized with Bgl II and transformed by electroporation in Pichia GS 115-competent cells, resulting in recombination of the plasmid at the AOX1 site of the genome to encode a nonfusion protein. The his4 GS115 should now be HIS4 Mut$^s$, and can be selected for a plating in histidine deficient plates followed by screening for retarded growth in methanol plates.

After 24 hours, positive colonies were harvested, pooled and re-plated into minimal plates. Since multiple copies of the construct are reported to confer resistance to high levels of GF18 we screened for "jackpot" clones by replica plating in increasing doses of GF18, as high as 4 mg/ml. After four days, approximately five colonies containing multiple copies of the gene were screened for expression levels of TIMP-3 in 5 ml cultures. The two clones showing the highest expression, T3-3 His+Mut$^s$ and T3-A His+Mut$^s$, were then used to inoculate 500 ml cultures, as was one clone containing pPIC9K vector alone as a control for background expression. Both T3-3 and T3-A produced a prominent protein band at app. 25 kDa by silver-stained SDS-PAGE, while vector control showed no band at the same molecular weight. Highly purified TIMP-3 was obtained by subsequent chromatography on a Progel-TSK G30000SWK HPLC column (Supelco) followed by SDS-PAGE and silver staining. Immunoblot analysis using TIMP-3 specific antibodies (Triple Point Biologics) demonstrated cross-reactivity of the 25 kDa band. Both T3-3 and T3-A were inhibitory when tested in the standard radiometric enzyme assay for MMP inhibition (Moses, M. A., et al., *Science* 248:1408–1410, (1990) and Moses, M. A., et al., *J. Cell Biol.* 119:475–482, (1992)).

We have followed the protocols described above for the expression of TIMP-3 with the exception being the cloning vector PCR II carried the C-terminal domain of human TIMP-2 consisting of loop 4–6 (Murphy, G., et al., *Biochemistry* 30(33):8089–8101, (1991); Willenbrock, F., et al., *Biochemistry* 32:4330–4337, (1993) and Nguyen, G., et al., *Biochemistry* 33:2089–2095, (1994)). The transformed colonies were screened for G418 resistance and one colony was found to be resistant to 1 mg/ml G418. This clone, T2C-11.1 was screened for expression levels along with five colonies resistant to various lower levels of G418. All clones were analyzed by SDS-PAGE followed by silver staining and a band at approximately 7,800–8,000 Da was detecting for each sample. Of all, T2C-11.1 produced the highest yield of expressed protein. T2C-11.1 was then used to inoculate 500 ml cultures, as was a clone transformed with vector alone for control. We purified the 7,800 Da protein using standard chromatographic strategies.

Figure 2:
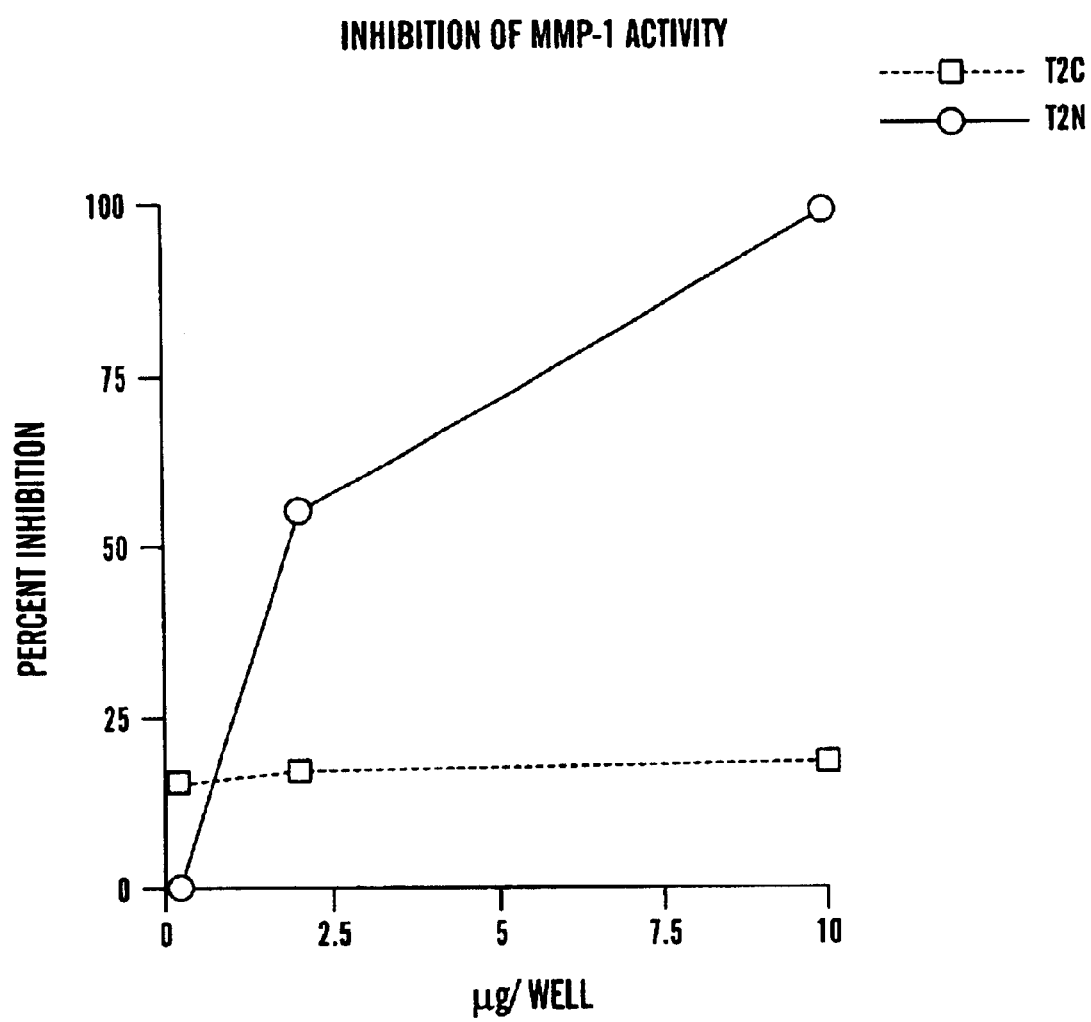
FIG. 2: MMP-1 activity assay.

The purified protein inhibited bFGF-stimulated EC proliferation in the bFGF stimulated EC proliferation assay (Moses, et al., *Science*, 248:1408–1410 (1990)) (FIG. 1) and inhibited neovascularization in vivo in the CAM assay. The purified protein did not inhibit MMP-1 activity (FIG. 2).

The invention has been described in detail with reference to preferred embodiments thereof. However, it will be appreciated that those skilled in the art, upon consideration of this disclosure, may make modifications and improvements within the spirit and scope of the invention.

The following references are incorporated herein by reference:

Liotta, L. A., et al. *Cell* 64:327–336, 1991.
Moses, M. A., et al. *Science* 248:1408–1410, 1990.
Moses, M. A., et al. *J. Cell Biol.* 119:475–482, 1992.
Ausprunk, D. H., et al. *Microvasc. Res.* 14:53–65, 1997.
Kalebic, T., et al. *Science* 221:281–283, 1983.
Moses, M. A., et al. *Science* 248:1408–1410, 1990.
Moses, M. A., et al. *J. Cell. Biochem.* 47:1–6, 1991.
Herron, G. S., et al. *J. Biol. Chem.* 261:2814–2828, 1986.
Montesano, R., et al. *Cell* 62:435–445, 1990.
Birkedai-Hansen, H. *Current Opinions in Cell Biol.* 7:728–735, 1995.
Matrisian, L. *Trends Genet.* 6:121–125, 1990.
Woessner, J. F. *Ann. N.Y Acad. Sci.* 732:11–21, 1994.
Docherty, A. J. P., et al. *Nature* 318:66–69, 1985.
Carmichael, D. F., et al. *Proc. Natl. Acad. Sci. USA* 83:2407–2411, 1986.
Moses, M. A., et al. *J. Cell. Biochem.* 47:230–235, 1991.
Murray, J. B., et al. *J. Biol. Chem.* 261:4154–4159, 1986.
Stetler-Stevenson, W. G., et al. *J. Biol. Chem.* 29:17374–17378, 1989.
Pavloff, N., et al. *J. Biol. Chem.* 267-17321–17326, 1992.
DeClerck, T. A., et al. *J. Biol. Chem.* 264:17445–17453, 1989.
Wilhelm, S. M., et al. *J. Biol. Chem.* 264:17213–17221, 1989.
Murphy, G., et al. *Biochemistry* 30(33):8097–8101, 1991.
Willenbrock, F., et al. *Biochemistry* 32:4330–4337, 1993.
Nyguyen, Q., et al. *Biochemistry* 33:2089–2095, 1994.
Murphy, G. et al. *Biochem. Biophys. Acta* 839:214–218, 1985.
Stricklin, G. P. *Collagen Relat. Res.* 6:219–228, 1986.
Tolley, S. P., et al. *Proteins: Struc., Fuct., Genet.* 17:435–437, 1993.
Howard, E. W., et al. *J. Biol. Chem.* 266:13064–13069, 1991.
O'Shea, M., et al. *Biochemistry* 31(42):10146–10151, 1992.
Bodden, M. K., et al. *J. Biol. Chem.* 269;18943–18952, 1994.
Williamson, R. A., et al. *Biochemistry* 33:11745–11759, 1994.
Hayakawa, T., et al. *FEBS Lett.* 298:29–32, 1992.
Goldberg, G. I., et al. *J. Biol. Chem.* 267:4583–4591, 1992.
Bodden, M. K. et al. *J. Biol. Chem.* 259:18943–18952, 1994.
Howard, E. W. et al. *J. Biol. Chem.* 266:13064–13069, 1991.
Mignatti, P., et al. *J. Cell. Bio.* 108:671–682, 1989.
Montesano, R. et al. *Cell* 42:469–477, 1985.
Murphy, A. N. et al. *J. Cell. Phys.* 157:351–358, 1993.
Takigawa, M., et al. *Biochem. Biophys. Res. Commun.* 171:1264–1271, 1990.
Johnson, M. D. et al. *J. Cell. Phys.* 160:194–202, 1994.
Stetler-Stevenson, W. G. *J. Biol. Chem.* 265(23):13933–13936, 1990.
White, C. E. et al. *Structure* 2:1003–1005, 1994.
Clare, J. J. et al. *Gene* 105:205–212, 1991.
Vedvick, T., et al. *J. Indust. Microbiol.* 7:199–202, 1991.
Sreekrishna, K., et al. *Biotechnology* 28:4117–4125, 1989.
Tschopp, J. J. *Biotechnology* 5:1305–1306, 1987.
Yanagisawa-Miwa, et al. *Science* 257:1401–1403, 1992.
Baffour, et al. *J. Vasc. Surg.*, 16:181–91, 1992.
Pu, et al. *J. Surg. Res,* 54:575–83, 1993.
Takeshita, et al. *Circulation,* 90:228–234, 1994.
Takeshita, et al. *J. Clin. Invest.,* 93:662–70, 1994.
Battegay, *J. Mol. Med.,* 73, 333–346, 1995.
Hanahan et al., *Cell,* 86, 353–364.
Folkman, J. et al. *J. Biol. Chem.* 267(16):10931–10934, 1992.
Folkman, J. *N. Engl. J. Med.,* 285:1182–1186, 1971.
Folkman, J. *N. Engl. J. Med.,* 333:1757–1763, 1995.
Sanger et al. *Proc. Natl. Acad. Sci. USA,* 74:136–140, 1986.
Lemelli. *Nature,* 227:680–685, 1970.
Connolly et al. *J. Anal. Biochem., J*52:136–140, 1986.
Polverini et al. *Methods Enzymol.,* 198:440–450, 1991.
Jain et al. *Nature Medicine,* 3:1203–1208, 1997.
Felgner et al. *J. Biol. Chem.,* 269:2550–2561, 1994.
Derossi et al. *Restor. Neurol. Neuros.,* 8:7–10, 1995
Abcallah et al. *Biol. Cell.,* 85:1–7, 1995

What is claimed is:

1. An isolated and purified antiangiogenic polypeptide selected from the group consisting of SEQ ID NO: 2, SEQ ID NO: 3, SEQ ID NO: 4, SEQ ID NO: 5, SEQ ID NO: 6 and SEQ ID NO: 7.

2. An isolated and purified antiangiogenic polypeptide comprising the amino acid sequence of SEQ ID NO: 2, but excluding the full sequence of human TIMP-2.

3. A pharmaceutical composition comprising an antiangiogenic polypeptide of claims 1–2 or a nucleic acid encoding such a polypeptide, in a therapeutically effective amount capable of inhibiting endothelial cell proliferation.

* * * * *